(12) United States Patent
Maaskamp et al.

(10) Patent No.: US 11,141,575 B2
(45) Date of Patent: Oct. 12, 2021

(54) LIPPED MEDICINAL APPLICATOR

(71) Applicants: Ryan Maaskamp, Scottsdale, AZ (US);
Armand Maaskamp, Scottsdale, AZ (US)

(72) Inventors: Ryan Maaskamp, Scottsdale, AZ (US);
Armand Maaskamp, Scottsdale, AZ (US)

( * ) Notice: Subject to any disclaimer, the term of this patent is extended or adjusted under 35 U.S.C. 154(b) by 0 days.

(21) Appl. No.: 16/783,382

(22) Filed: Feb. 6, 2020

(65) Prior Publication Data

US 2020/0269026 A1    Aug. 27, 2020

Related U.S. Application Data

(60) Provisional application No. 62/810,501, filed on Feb. 26, 2019.

(51) Int. Cl.
*A61M 31/00* (2006.01)

(52) U.S. Cl.
CPC ..... *A61M 31/00* (2013.01); *A61M 2210/1067* (2013.01)

(58) Field of Classification Search
CPC .......... A61M 31/00; A61M 2210/1067; A61M 31/007; A61B 2017/3452
See application file for complete search history.

(56) References Cited

U.S. PATENT DOCUMENTS

| | | | |
|---|---|---|---|
| 3,109,427 A * | 11/1963 | Davidson | A61M 31/00 604/212 |
| 3,667,461 A | 6/1972 | Zamarra | |
| 4,906,239 A * | 3/1990 | Bruhl | A61H 21/00 604/275 |
| 5,695,481 A | 12/1997 | Heinzelman et al. | |
| 5,843,043 A * | 12/1998 | Markus | A61M 31/00 604/239 |
| 7,090,654 B2 | 8/2006 | Lotito et al. | |
| 7,125,394 B2 | 10/2006 | Berman et al. | |
| 7,322,953 B2 | 1/2008 | Redinger | |
| 7,465,295 B2 | 12/2008 | Bergeron et al. | |
| 8,092,415 B2 | 1/2012 | Moehle et al. | |

(Continued)

OTHER PUBLICATIONS

Zakharchenk et al., "Safety and efficacy of superior rectal . . . ", 2016, Diagnostic and Interventional Imaging, http://dx.doi.org/10.1016/j.diii.2016.08.002.*

*Primary Examiner* — Bhisma Mehta
*Assistant Examiner* — John J Crawford
(74) *Attorney, Agent, or Firm* — Kenneth Altshuler

(57) ABSTRACT

Described is an anal medicinal applicator that generally comprises a base, a medicinal cream receiving port in the base, a shaft and at least one longitudinal slot. The longitudinal slot extending along an axis from the base and terminating at a distal end. The at least one longitudinal slot extending along a portion of the shaft, the receiving port, the shaft and the at least one longitudinal slot defining an unobstructed pathway. The longitudinal slot defined by a leading slot edge, a trailing slot edge, a proximal slot edge, and a distal slot edge, the leading slot edge and the trailing slot edge are longer than the proximal slot edge and the distal slot edge. A lip protrudes from the shaft along at least a portion of the leading slot edge it is configured and arranged to cause a tenting effect of the inner intestinal wall when the anal medicinal applicator is deployed in an anus.

20 Claims, 12 Drawing Sheets

(56) References Cited

U.S. PATENT DOCUMENTS

| | | |
|---|---|---|
| 9,132,262 B2 | 9/2015 | Berman et al. |
| 2014/0074051 A1* | 3/2014 | Berman ................ A61M 31/00 604/279 |

* cited by examiner

LIPPED MEDICINAL APPLICATOR

CROSS-REFERENCE TO RELATED APPLICATIONS

This application claims priority to and the benefit of U.S. provisional Patent Application No. 62/810,501 entitled: Lipped Medicinal Applicator, filed on Feb. 26, 2019.

FIELD OF THE INVENTION

The present embodiments are generally directed to a medicinal dispenser probe with a lip for improved ease of dispensing medicinal cream in an anal canal.

DESCRIPTION OF RELATED ART

Certain medical ailments afflict regions of human anal canals. In some instances, these medical ailments (such as infections, viral related blisters, cancers, fissures or some other pathological pain or disease) are treatable with a medicinal cream when applied to the surface tissue of the anal canal. Presently, such medicinal creams are often applied manually in the anal canal by spreading the cream on the anal canal surface via a finger. One problem with using a finger to spread the medicinal cream is that it often requires the help of a second person because it is difficult to auto apply (i.e., self-apply) the medicinal cream. Accordingly, applicators for dispensing a medicinal cream to anal canals exist so that people can independently apply (auto apply) medicinal cream to themselves (their anal canal) without the help of a second person.

FIG. 1A, in view of FIG. 1B, illustratively depicts a line drawing of a prior art applicator for auto application of a medicinal substance in an anal canal. As shown, the applicator 100 possesses a handle 106, a shaft 110 that extends from the handle 106 and terminates in a rounded dome 104 at a distal end of the applicator 100. As shown, the rounded dome 104 has a diameter that never exceeds the diameter of the shaft 110 in order to facilitate easy insertion in a human anus. The proximal end 102 of the applicator 100 is adapted to receive a medicinal cream (or other viscous material/s) by way of an aperture 101. There is an unobstructed pathway 121 (see FIG. 1B) between the aperture and two slots 120, the two slots are axially located along the length of the shaft 110. As a note, the cross-section of the outer physical surface 119 (as opposed to the phantom circular shape 117) does not extend beyond, or outside the boundary of, the circular shape 161 (FIG. 1B). The applicator 100 is universal to any natural opening of the anatomy of a human body including vaginal openings and the anal openings. Accordingly, the applicator 100 is nonspecific to any particular anatomy of any specific opening of a human body.

FIG. 1B illustratively depicts a line drawing of the cross-section of the prior art applicator shaft along the cut-line A-A 160 of the shaft 110. As shown, the shaft 110 has two openings 120 through which the medicinal cream can be expelled from the applicator 100. As shown, the cross-section of the outer surface of the shaft 110 at the longitudinal slot 120 maps to a circular shape 161. Moreover, the cross-section of essentially any location along the shaft 110 maps to a circular shape whereby the physical surface at the cross-section is greater than 50% (the physical surface depicted by the shaded regions 110 of the cross-section 160, mapped projected circular region depicted by the dashed circle 161). As previously mentioned, because the shaft 110 maps to a circular shape, the applicator 100 is nonspecific to any particular anatomy of any specific opening of a human body which makes the applicator 100 deficient for applying medicinal cream to any specific contours of an orifice, such as in an anal canal, for example. In other words, the circular shape and size of the shaft makes it difficult to impossible to reach into folds within an anal canal.

In practice, the applicator 100 can be gripped via the handle 106, inserted through the anus and into the anal canal whereby medicinal cream can be forced through the aperture 101 and out through the slots 120. While the medicinal cream is being pushed out of the slots when the shaft is deployed in the human anal canal, a person can rotate the shaft 110 by way of turning the handle 106 to coat the surface of the anal canal. Because the applicator 100 is not specific to any particular anatomy of any specific opening of a human body, the cross-section of the shaft 110 maps to a circular profile or shape 161.

FIG. 1C illustratively depicts a line drawing of a syringe 140 and applicator 100 connected to deploy the medicinal cream into the anal canal. The applicator 100 is shown fixedly attached with a syringe 140 by way of a connector (such as a screw interface or other mechanical connecting means) at the interface between the proximal end 102 and syringe exit port end 152. In this illustration, the syringe 140 is partially depressed i.e., the plunger seal 142 is displaced partway down barrel/tube 144. In practice, a person squirting medicinal cream 150 either into their anal canal (self-administering) or someone else's anal canal will grip the syringe barrel 144 with their hand and depress the plunger top 148 in the direction of arrow 155. By depressing the plunger top 148, the plunger piston 146 will physically push the medicinal cream 150 via the plunger seal 142 through the unobstructed pathway 130 and out the longitudinal slot/s 120 and into the anal canal, as shown by arrow 156. While the medicinal cream 150 is being pushed out of the slots 120 when the shaft 110 is deployed in a human anal canal, a person can rotate the shaft 110 by way of turning the handle 106 (either clockwise or counterclockwise) to coat the surface of the anal canal.

FIG. 1D illustratively depicts medicinal dispenser tube 170 that can be used with the applicator 100 as shown. The advantage of the medicinal dispenser tube 170 is that it is far less expensive to produce and distribute then the syringe 140 of FIG. 1C. The medicinal dispenser tube 170 possesses a flexible body 175 that can be manually squeezed much like a tube of toothpaste. The medicinal dispenser tube 170 further comprises a rigid or semi rigid top 174 that has a mail screw end 176 configured to fixedly connect to the proximal end 102 of the applicator 100. When squeezed in the direction of the arrows 172, the medicinal cream 150 is expelled through the unobstructed pathway 130 and out the slots 120 of the applicator 100 as shown by arrow 156. Though inexpensive, one of the disadvantages of the medicinal dispenser tube 170 is that it requires reasonable gripping strength to squeeze the medicinal cream 150 into the anal canal. The syringe 140 provides better mechanical advantage in deploying the medicinal cream 150 into the anal canal, however depending on the viscosity of the medicinal cream 150 depressing the plunger top 148 can still require a fair amount of hand strength. Both the syringe 140 and medicinal dispenser tube 170 may prove difficult for a person attempting to self-administer medicinal cream 150 if they lack sufficient strength to actuate the syringe 140 or to squeeze the medicinal dispensing tube 170.

It is to innovations related to this subject matter that the claimed invention is generally directed.

SUMMARY OF THE INVENTION

The present embodiments are generally directed to a medicinal dispenser probe with a lip for improved ease of for auto applying medicinal cream in an anal canal.

Certain embodiments of the present invention contemplate an anal medicinal applicator embodiment, an anal medicinal applicator can comprise: a base; a medicinal cream receiving port in the base; a shaft extending along an axis from the base and terminating at a dome cap, at least one longitudinal slot extending along a portion of the shaft, the receiving port, the shaft and the at least one longitudinal slot defining an unobstructed pathway, the longitudinal slot defined by a leading slot edge, a trailing slot edge, a proximal slot edge, and a distal slot edge, the leading slot edge and the trailing slot edge are longer than the proximal slot edge and the distal slot edge; and a lip protruding from the shaft along and in-line with at least a portion of the leading slot edge.

Other certain embodiments of the present invention contemplate a method for using an anal medicinal applicator embodiment is envisioned to comprise steps for: providing the anal medicinal applicator that comprises a base possessing a receiving port, a shaft extending along an axis from the base to a distal end, a probe tip at the distal end, at least one longitudinal slot extending along a portion of the shaft, an anus abutting stop-plate delineating the base and the shaft, the anus abutting stop-plate extending radially beyond the shaft, and an unobstructed pathway extending from the receiving port through the anus abutting stop plate and through a portion of the shaft to a distal portion of the at least one longitudinal slot that is closest to the distal end, the longitudinal slot defined by a leading slot edge, a trailing slot edge, a proximal slot edge, and a distal slot edge, the leading slot edge and the trailing slot edge are longer than the proximal slot edge and the distal slot edge, and an intestinal wall tenting lip protruding from the shaft along at least a portion of the leading slot edge; inserting the shaft through an anus and into a rectum only as far as the anal abutting stop-plate; after the inserting step, dispensing a viscous material through the receiving port and out through the at least one longitudinal slot; and after the inserting step, rotating the anal medicinal applicator about the axis.

In yet another embodiment of an anal medicinal dispenser, the medicinal dispenser can comprise: an anal shaft extending from a handle to an anal tip; an anus abutting stop plate extending essentially radially from the anal shaft, the anus abutting stop plate delineating the handle from the anal shaft; at least one longitudinal slot extending longitudinally along the anal shaft; an intestinal wall tenting lip protruding from the anal shaft, the intestinal wall tenting lip extending longitudinally along an edge of the longitudinal slot; and a medicinal cream pathway extending between and including a) a receiving port in the handle and b) the longitudinal slot.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving similar uses of anal enhancements for use in dispensing medicinal cream anally. In what follows, similar or identical structures may (and may not) be identified using identical callouts.

Described herein are embodiments of an anal medicinal applicator that possesses a base, a medicinal cream receiving port in the base, a shaft and at least one longitudinal slot. The longitudinal slot extending along an axis from the base and terminating at a distal end. The longitudinal slot/s extending along a portion of the shaft, the receiving port, the shaft and the longitudinal slot/s—all defining an unobstructed pathway. The longitudinal slot is essentially defined by a leading slot edge, a trailing slot edge, a proximal slot edge, and a distal slot edge. The leading slot edge and the trailing slot edge are longer than the proximal slot edge and the distal slot edge. In certain embodiments, the longitudinal slot is more or less a rectangular opening. Along at least a portion of the leading slot edge is a lip that protrudes from the shaft. The lip is configured and arranged to cause a tenting effect of the inner intestinal wall when the anal medicinal applicator is deployed, or otherwise inserted in an anus.

Figure 1A:
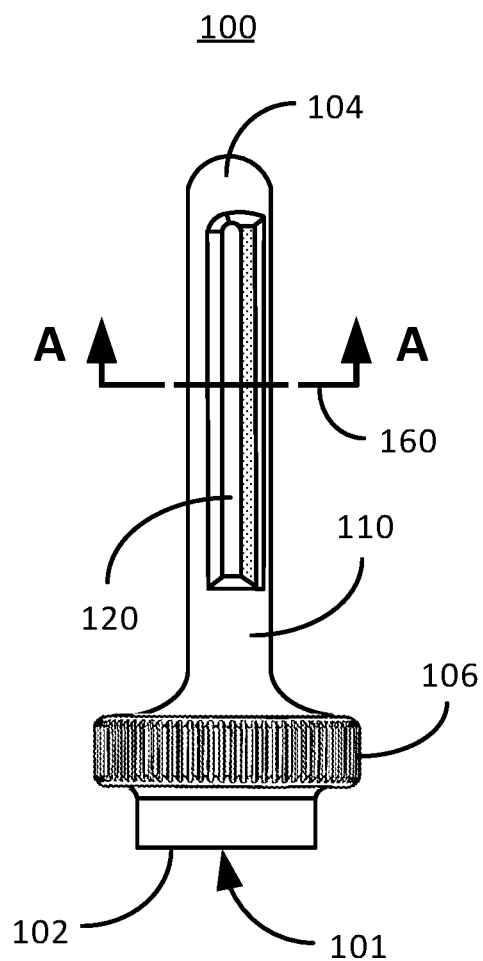
FIG. 1A illustratively depicts a line drawing of a prior art applicator for auto application of a medicinal substance in an anal canal.
Figure 1B:
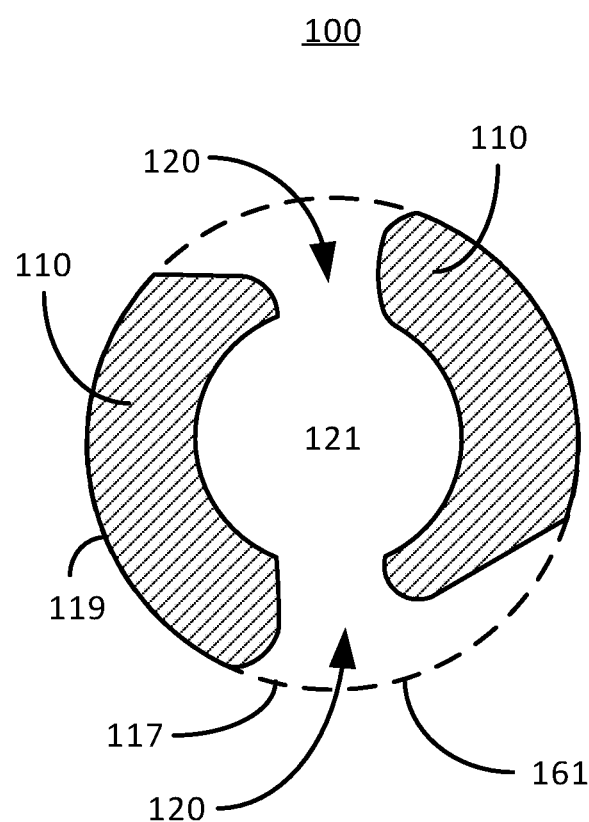
FIG. 1B illustratively depicts a line drawing of the cross-section of the prior art applicator shaft along the cut-line A-A of the shaft.
Figure 1C:
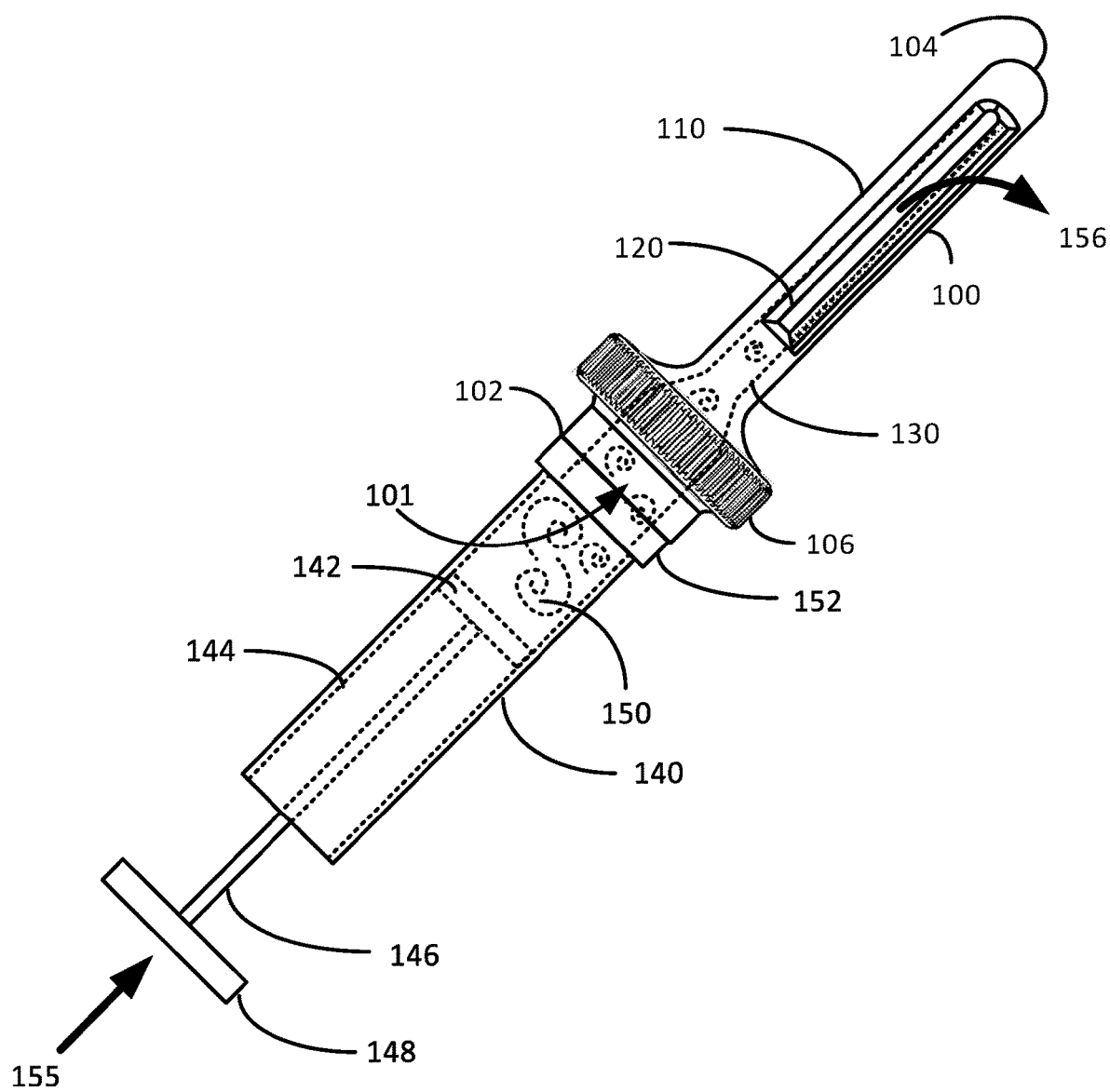
FIGS. 1C and 1D illustratively depict line drawings of a prior art angle applicator for dispensing syringe and dispensing tube, respectively.
Figure 1D:
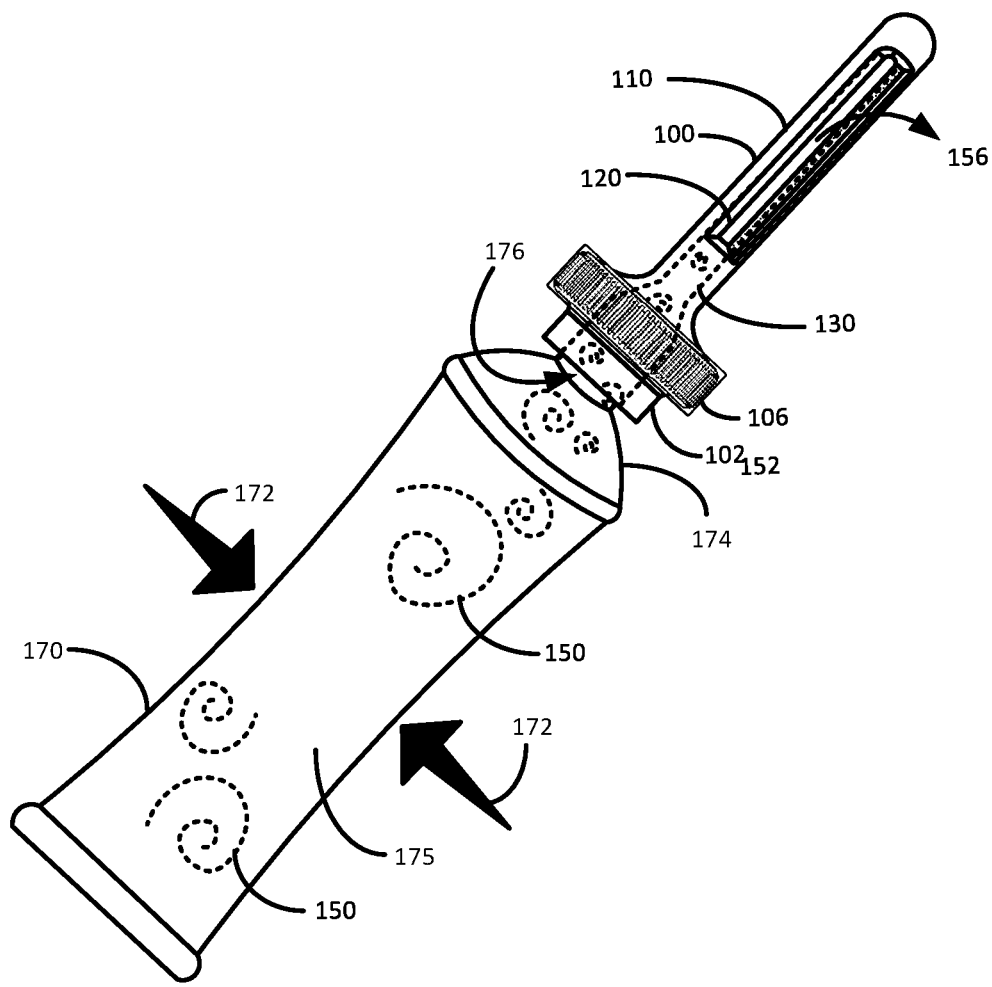
Figure 2A:
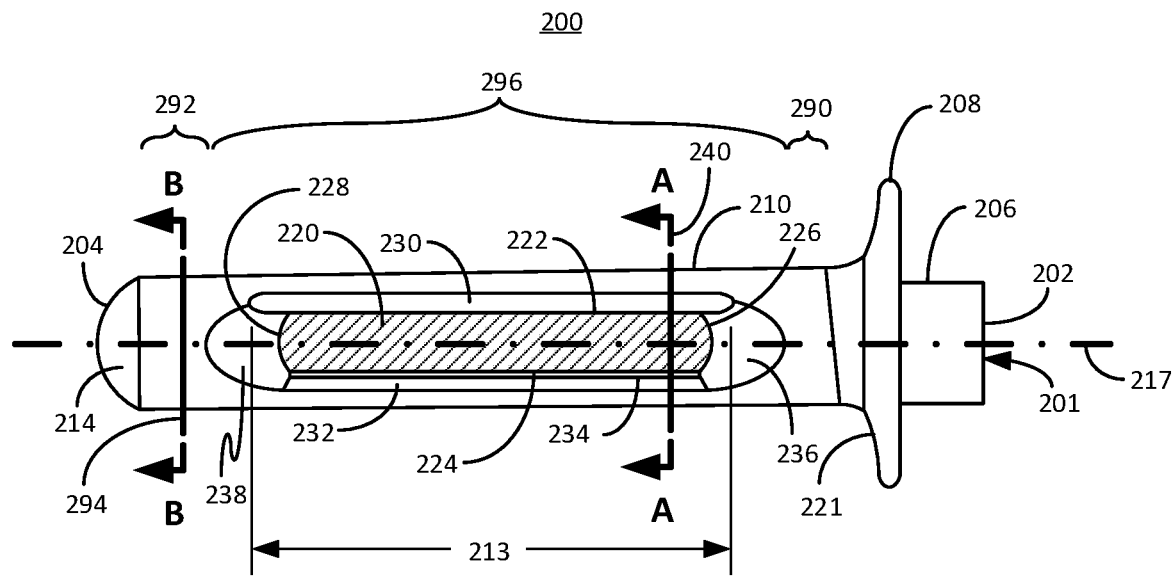
FIGS. 2A-2C illustratively depict different line drawing views of an anal medicinal applicator embodiment consistent with embodiments of the present invention.
Figure 2B:
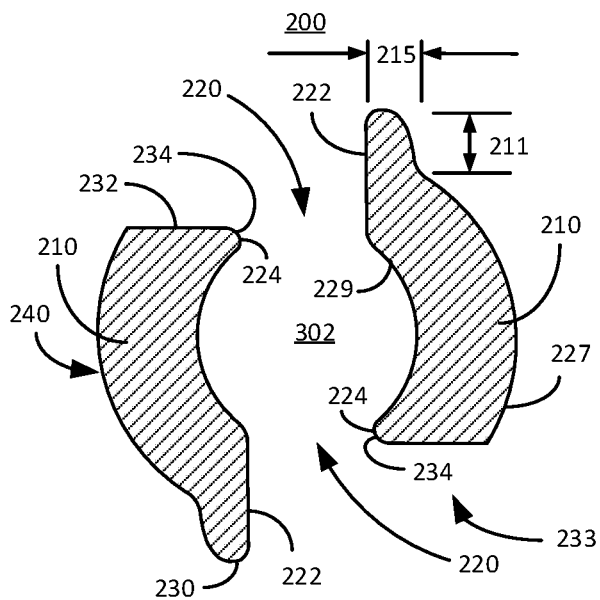
Figure 2C:
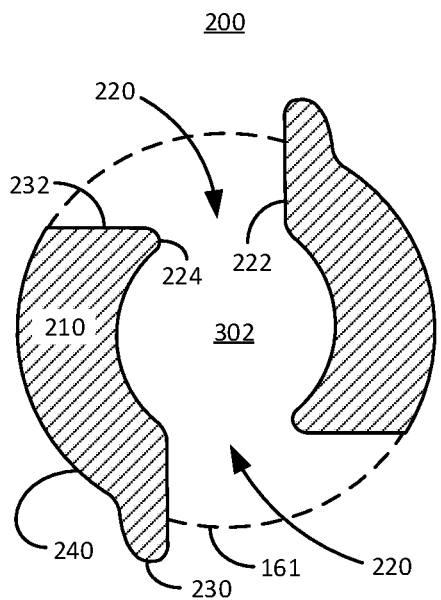

FIGS. 2A-2C illustratively depict different line drawing views of an anal medicinal applicator embodiment 200 consistent with embodiments of the present invention. FIG. 2A shows a side view illustration of the anal medicinal applicator 200 generally comprising a base 206 and a shaft 210 separated by an anal (or anus) abutting stop-plate 208, also simply called a stop-plate herein. In more detail, the anal medicinal applicator 200 comprises a base 206 and a shaft 210 that extends along an axis 217 from the base 206 and terminates at a distal end 204. In this figure, the base 206 is essentially a cylinder that defines the proximal end 202 of the anal medicinal applicator 200. The proximal end 202 comprises a medicinal cream receiving port 201 which is essentially an aperture leading into an unobstructed pathway 302 (shown in FIGS. 3A and 3B). The unobstructed pathway 302 passes through the base 206 and into the shaft 210 terminating at the at least one slot 220, discussed in more detail infra. Certain embodiments envision the longitudinal slots as curved, spiraled, or some other shape. The stop-plate 208 possesses a sloped surface 221 that transitions into the shaft 210. The sloped surface 221 is adapted to butt up against an anus (not shown) when the anal medicinal applicator 200 is inserted in an anal canal. The stop-plate 208 extends radially from the axis 217 beyond the shaft 210 and essentially confines only the elements (shaft 210, dome 214, etc.) of the anal medicinal applicator 200 that are distal to the sloped surface 221 as being capable of going inside of an anal canal. In other words, the anus abutting stop-plate 208 prevents the base portion 206 from being pushed inside of the anal canal. The anal shaft 210 comprises an anal region of the shaft 210, which is the portion of the shaft that goes into a human anal canal. In this embodiment is the entire shaft 210 that is distal to the anal abutting stop-plate 210.

With more detail to the shaft portion 210, a pair of opposing longitudinal dispensing slots (or in certain embodiments, just one longitudinal slot) 220 extend along a shaft portion 296 of the shaft 210 in-line with the axis 217 as shown. In the present embodiment, there is a proximal shaft region 290 and a distal shaft region 292 that are devoid of the shaft portion 296 that includes the longitudinal slots 220. The longitudinal slots 220 essentially serve as exit apertures that dispense medicinal cream, or some other viscous material, in an anal canal. The shaft 210 terminates at the dome 214 that defines the distal end 204 of the anal medicinal applicator 200. In this embodiment, the dome 214 is essentially a semi-spherical knob at the distal end 204 of the shaft 210, though other shapes at the dome end are envisioned.

As presented in this view, the longitudinal slot 220 is defined having a leading slot edge 222, a trailing slot edge 224, a proximal slot edge 226 and a distal slot edge 228. Hash lines form a shaded region indicating that the longitudinal slot 220 is an aperture. In the present embodiment, the longitudinal slot 220 are essentially a rectangular aperture with slight outwardly curved proximal and distal slot edges 226 and 228. The leading slot edge 222 and the trailing slot edge 224 are longer than the proximal slot edge 226 and the distal slot edge 228. The leading slot edge 222, the trailing slot edge 224, the proximal slot edge 226 and the distal slot edge 228 are not limited to being linear or parallel. In the present embodiment, longitudinal slot 220 is recessed in the cylindrical shaped shaft 210 with a proximal chamfer 236 sloping into the proximal slot edge 226 and a distal chamfer 238 sloping into the distal slot edge 228, as shown. A flat trailing edge surface 232 leads into the trailing slot edge 224 via a softening roll-off 234. The softening roll-off 234 is simply provided for reference and is a non-limiting embodiment of the present invention.

An embodiment of a lip 230 is depicted running along the length of the leading slot edge 222, i.e., having a lip length 213. The lip 230 extends outwardly from (beyond) the profile of the shaft 210 and the chamfers 236 and 238 in what is shown as the lip height 211. In certain embodiments, the lip 230 is considered an appendage extending from the surface of the shaft 210. A cut-line A-A 240 defines a cross-sectional view of the shaft 210 strictly at the longitudinal slot 220 without the view of any other elements beyond the cut-line A-A 240.

FIG. 2B illustratively depicts a cross-section of the anal medicinal applicator 200 along the cut-line A-A 240, which is an orthogonal slice along the shaft 210 (center running axis not shown but consistent with FIG. 2A) over the longitudinal slots 220. As shown in this embodiment, there are two longitudinal slot apertures 220 defined by the leading slot edge 222 and the trailing slot edge 224, through which medicinal cream can be made to flow out. An embodiment of a raised lip 230 protrudes from the shaft cross-sectional profile 240 at the leading slot edge 222. An embodiment of a flat trailing edge surface 232 spans between the shaft outer surface 227 and the inner surface 229 of the pathway (core) 302 at the trailing edge 233 as shown. Here, the flat trailing edge surface 232 leads into the trailing slot edge 224 via a softening roll-off 234. Certain embodiments contemplate the shaft 210 rotating clockwise with respect to the cross-section 240 whereby the medicinal cream 150 preferentially flows out along the flat trailing edge surface 232 into the anal canal. Though the present embodiment depicts the cross-section 240 of the shaft 210 mapping to a circle, other embodiments contemplate the shaft mapping to other cross-sectional shapes and configurations without departing from the scope and spirit of the present invention. Accordingly, certain other embodiments envision that various cross-sectional shapes that do not map to a circle are defined in the absence a raised lip embodiment (meaning a raised lip embodiment does not define the map of a cross-sectional shape). Certain embodiments envision that the raised lip 230 extends outwardly from the cross-sectional shape, which in certain embodiments has a lip height 211 of greater than 1 mm and in certain embodiments is greater than 3 mm. Certain other embodiments contemplate the lip 230 with a lip width 215 being greater than 5 mm while some embodiments envision the lip width of being less than 7 mm wide where the lip 230 extends past the shaft 210. Yet other embodiments do not consider such dimensional constraints of a lip width 215 or lip height 211.

FIG. 2C is a line drawing showing a cross-section of the anal medicinal applicator 200 at both the cut-line's A-A 240 and B-B 292 consistent with embodiments of the present invention. The shaded region of the shaft 210 is along the cut-line A-A showing the longitudinal slots 220. The dashed region 119 illustratively depicts the shaft outer profile in the regions 290 and 292 that do not include the shaft portion 296 (the shaft portion 296 includes the longitudinal slots 220, and the chamfers 236 and 238). The dashed outer profile 119 is essentially the shape of the shaft if the longitudinal slots 220 and lips 230 were not present. As shown, each of the "raised" lips 230 are associated with the leading slot edge 222. The raised lips 230 protrude from the shaft outer profile 119, as shown. In contrast, each of the trailing slot edges 224 are either in-line or recessed from the shaft outer profile 119.

Figure 3A:
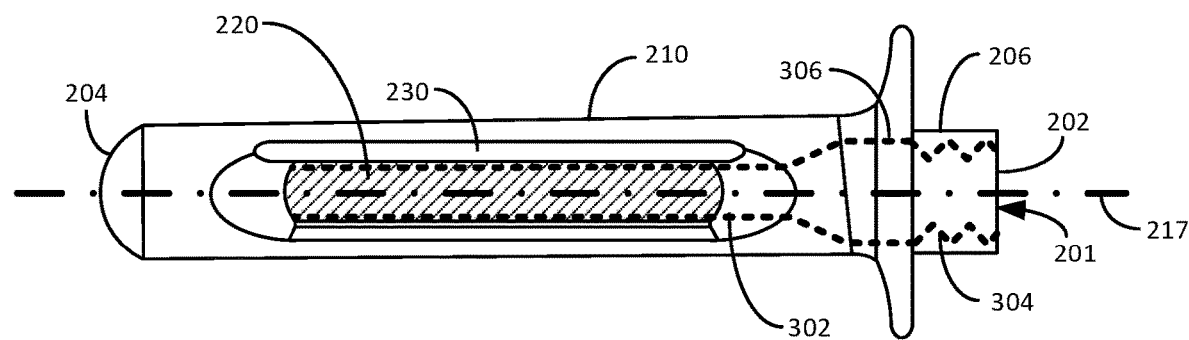
FIGS. 3A and 3B illustratively depict a side view of the anal medicinal applicator with greater detail to the unobstructed pathway system with embodiments of the present invention.
Figure 3B:
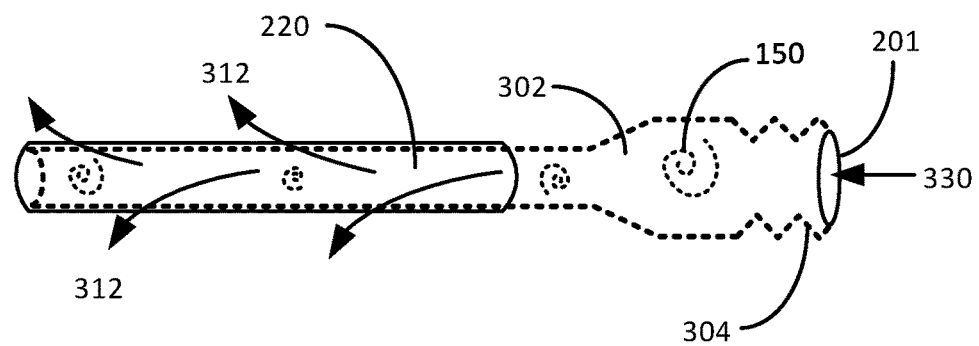

FIGS. 3A and 3B illustratively depict a side view of the anal medicinal applicator 200 with greater detail to the unobstructed pathway system 302 with embodiments of the present invention. Similar to FIG. 2A, FIG. 3A depicts the side view of the anal medicinal applicator 200 with the unobstructed pathway 302, shown by dotted lines. The unobstructed pathway 302 comprises an inlet port (receiving port) 201 in the proximal end 202, illustratively shown by the arrow 201. The inlet port 201 is adapted to receive medicinal cream from a syringe 140, medicinal cream dispensing tube 170 or other cream (viscous material) dispensing device capable of dispensing cream without departing from the scope and spirit of the present invention. The inlet port 201 is configured and arranged to cooperate with an outlet port of a medicinal cream dispensing device, which in the present embodiment is by way of a threaded channel 304. Other embodiments envision some other mechanical means to lock or otherwise form a cooperating relationship between the anal medicinal applicator 200 and a medicinal cream dispensing device. The unobstructed pathway 302 passes through the hub of the base 206, through a passageway in the stop-plate 306, and out through the at least one longitudinal dispensing slot 220. Certain embodiments contemplate the unobstructed pathway 302 symmetrically in-line with the axis 217.

FIG. 3B illustratively depicts an isolated view of the unobstructed pathway 302 of FIG. 3A whereby the arrow 330 illustratively shows the medicinal cream 150 entering in the inlet/receiving port 201 and exiting the at least one longitudinal dispensing slot 220 (which is part of the unobstructed pathway 302) as shown by the curved arrows 312. In practice, the medicinal cream 150 (as illustratively depicted by the arrows 330 and 312) is made to flow into the anal canal when the anal medicinal applicator 200 is deployed in the anal canal accordingly.

Figure 4:
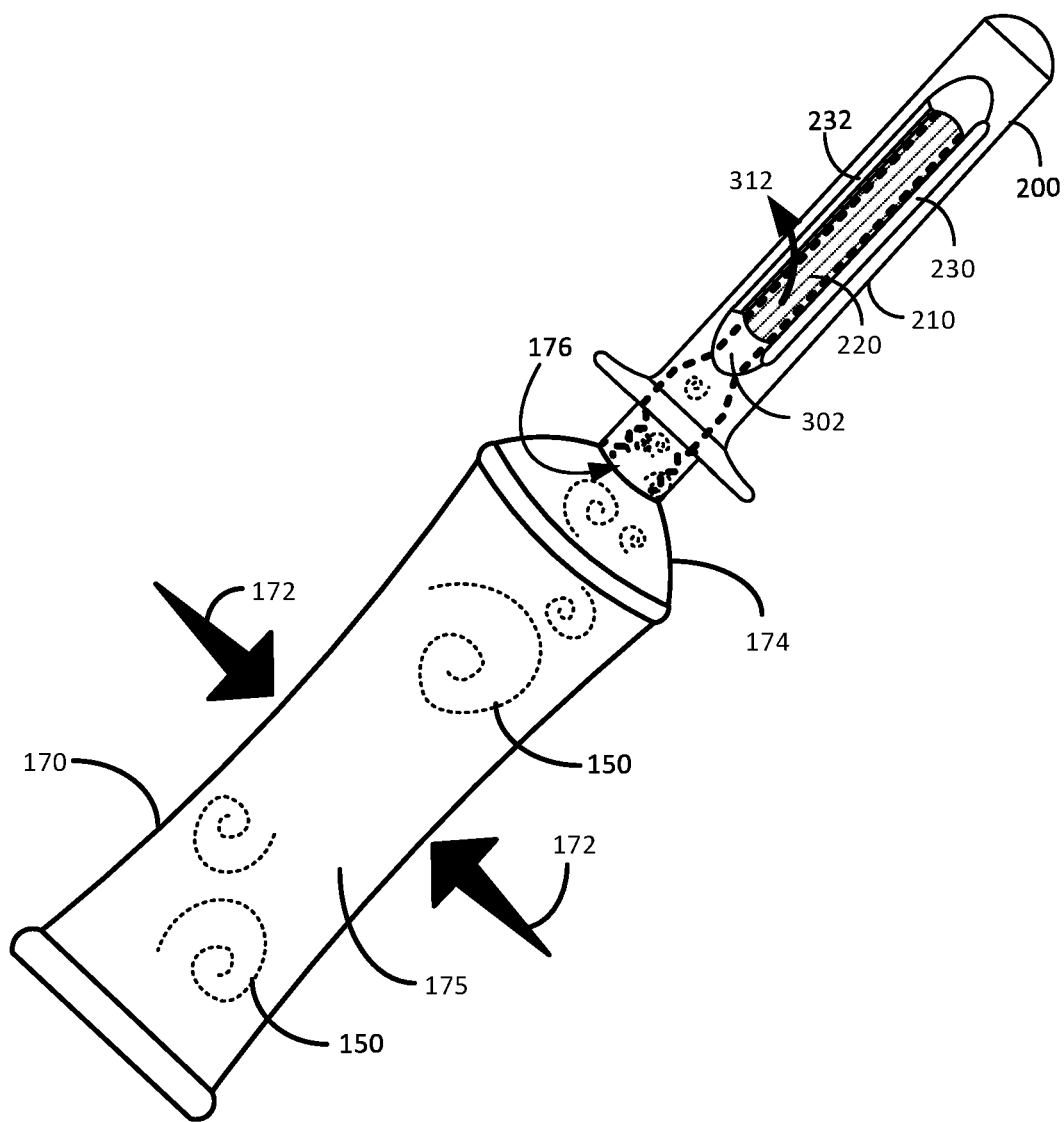
FIG. 4 illustratively depicts a drawing of an anal medicinal applicator cooperating with a medicinal dispenser tube consistent with embodiments of the present invention.

FIG. 4 illustratively depicts a drawing of an anal medicinal applicator cooperating with a medicinal dispenser tube filled with medicinal cream consistent with embodiments of the present invention. The anal medicinal applicator 200 is shown fixedly attached with a medicinal dispenser tube 170 by way of a connecting element, which in the present embodiment is a threaded male/female connector at the threaded portions 304 and 176. Of course, other attachment configurations known to those skilled in the art can be used within the scope and spirit of the present invention, such as a clip relationship or other attachment relationship. In this example, the dispenser tube 170 is partially squeezed at the flexible tube body region 175 as depicted by the arrows 172. The flexible tube body region 175 can be any flexible material known to those skilled in the art including a flexible polymer, metal foil, fabric, just to name several examples. In practice, a person squirting medicinal cream 150 either into their anal canal (self-administering), or someone else's anal canal, will grip the flexible tube body 175 with their hand and squeeze the tube body 175 in the direction of arrow 172. By squeezing the tube body 175, the medicinal cream 710 will be physically pushed through the unobstructed pathway 302 and out from the longitudinal slot/s 220 and into the anal canal, as shown by arrow 312. As a skilled artisan will appreciate, the dispenser tube 170 is hardly exhaustive of the number of medicinal cream dispenser devices known to those skilled in the art that are well adapted to cooperate with the medicinal applicator embodiments described herein or otherwise understood within the scope and spirit of the present invention. The lip 230 and the flat trailing edge surface 232 make it considerably easier to squeeze the dispenser tube 170 as will be discussed next.

Figure 5A:
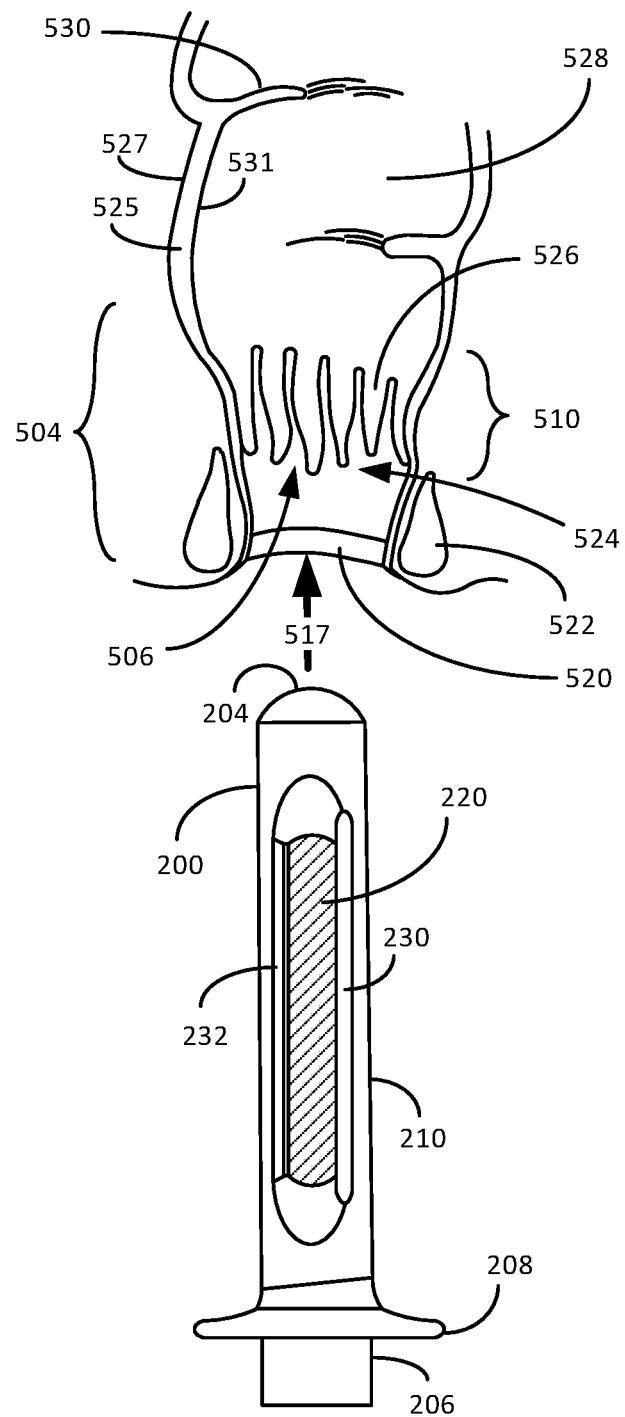
FIG. 5A depicts the anal medicinal applicator embodiment about to be inserted in anal canal shown by the arrow pointing to opening of the anus consistent with embodiments of the present invention.

FIG. 5A depicts the anal medicinal applicator 200 about to be inserted in the anal canal 504 (shown by the arrow 517 pointing to the opening of the anus 520). An outer intestinal wall 527 and an inner intestinal wall 531 that are boundaries defining the mucosa and muscle layers 525 define this portion of the intestine, which includes the anal canal 504. The general anatomy of the anal canal 504 includes a transition zone 510 that illustratively shows corrugations/folds formed by anal crypts 506 and anal columns 526. The dentate line 524 defines the start of the corrugations/folds in the anal canal 504. For reference, the internal anal sphincter 522 that constricts the anus 520 is on either side of the anus 520, further up the anal canal 504 is the rectum 528 and the levator ani muscle 530. This is a very coarse artistic impression of the intestine and anal canal that meets the resolution needed for explanation for this disclosure but may lack the exact anatomical structures and morphologies known to those skilled in the art.

Figure 5B:
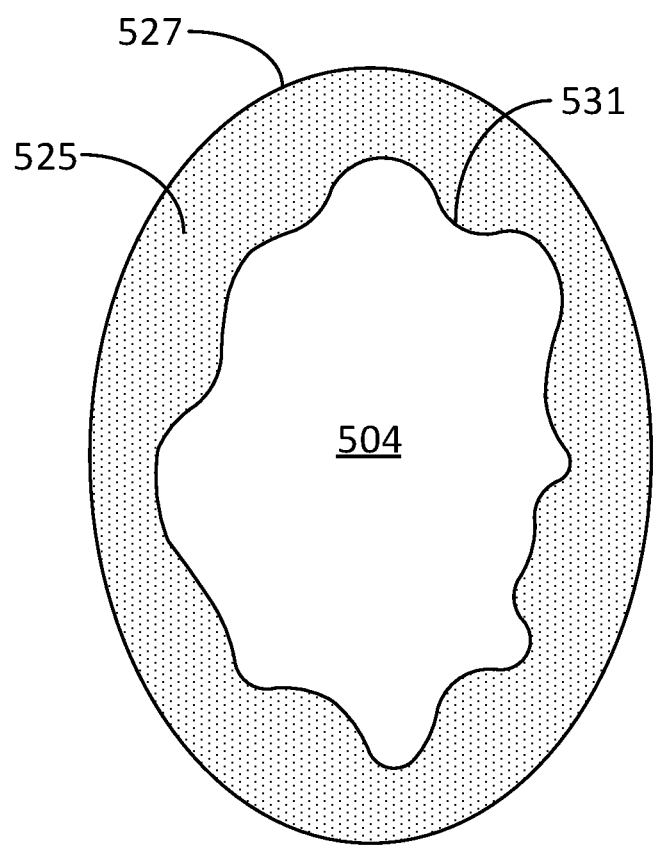
FIG. 5B illustratively depicts a line drawing of a cross-section of an anal canal when in a state devoid of a probe or other object therein.

FIG. 5B illustratively depicts a line drawing of a cross-section of an anal canal 504 when in a state devoid of a probe or other object therein. For reference, shown are the mucosa and muscle layers 525, depicted as a pixelated pattern fill, defined between the outer intestinal wall 527 and the inner intestinal wall 531. This is a very coarse artistic impression of the intestine and anal canal that meets the resolution needed for explanation for this disclosure but may lack the exact anatomical structures and morphologies known to those skilled in the art.

Figure 5C:
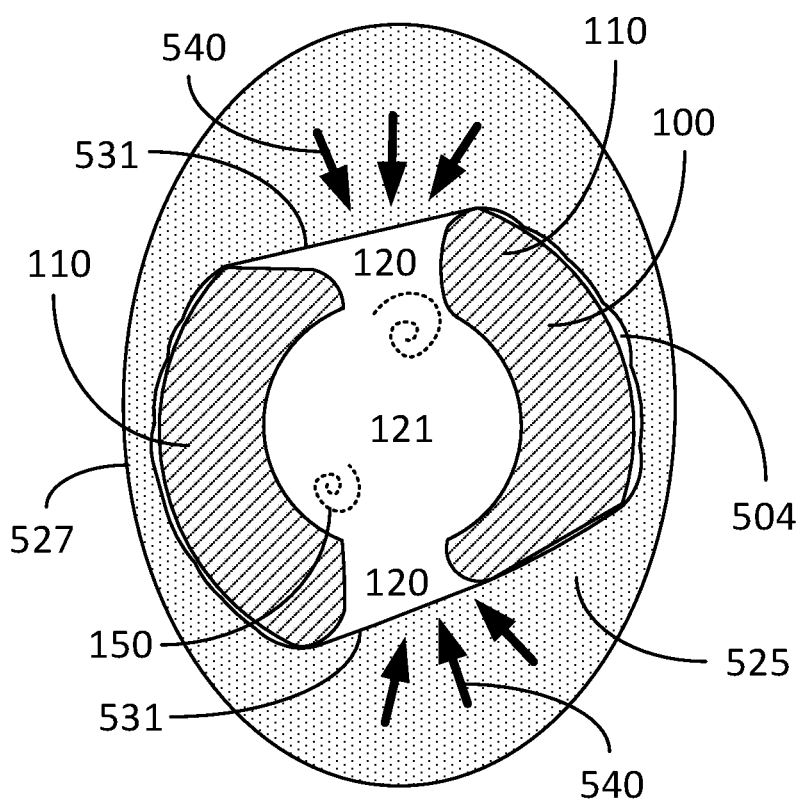
FIG. 5C illustratively depicts an artistic rendition of the described shortcomings of a prior art applicator when inserted in an anal canal.

FIG. 5C illustratively depicts an artistic rendition of the described shortcomings of a prior art applicator 100 when inserted in an anal canal 504. More specifically, because essentially no portion of the prior art applicator 100 physical extends beyond the boundary of the circular shape 161 of the cross-section of the prior art applicator 100, the inner intestinal wall 531 stretches across the slot apertures 120 as shown. Accordingly, the intestinal wall 530 essentially collapses around slot apertures 120 thereby blocking the slot apertures 120 from easily expelling the medicinal cream 150 (see arrows 540). Because the intestinal wall 530 resists the flow of medicinal cream 150 by minimizing the exit area of the longitudinal slot 120, the prior art applicator 100 is best suited for use with an expensive and cumbersome syringe 140 that provides more medicine ejection force than a tube. As previously discussed, it is easier to produce more ejection force using the syringe plunger system 142, 146 and 148 than it is to use a tube 170. Hence, the prior art applicator 100 is a suboptimal solution for use with a less expensive and easier to use medicinal dispenser tube 170, for example, because it requires substantial grip strength of a person's hand. For some people, the grip strength required to overcome the blocking force 540 at the longitudinal slot aperture 120 is too great to effectively use a medicinal dispenser 170.

Figure 5D:
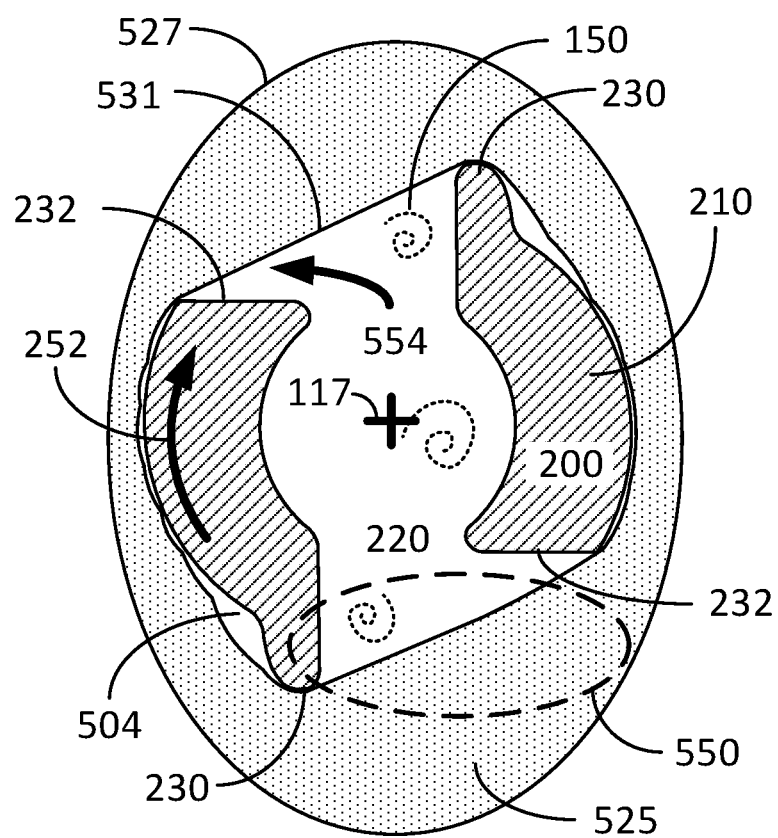
FIG. 5D illustratively depicts an artistic rendition of an embodiment of an anal medicinal applicator consistent with embodiments of the present invention.

FIG. 5D illustratively depicts an artistic rendition of an embodiment of an anal medicinal applicator deployed in an anal canal 504 consistent with embodiments of the present invention. As shown, the anal medicinal applicator 200 is inserted in an anal canal 504 whereby the lip 230 associated with the applicator 200 protrudes beyond the outside boundary (as earlier defined) of the circular shape of the shaft 210. The lip 230 provides a "tenting" effect that stretches the inner intestinal wall 531 away from the center axis 217 [see FIG. 6] thereby creating additional space 550 (shown by the dashed ellipse 550) for expelling the medicinal cream 150 from the longitudinal slot 220. Certain embodiments contemplate rotating the shaft 210 clockwise, in the direction of the curved arrow 252, which causes the medicinal cream 152 more easily flow over the flat trailing edge surface 232, as shown by arrow 554.

Figure 6:
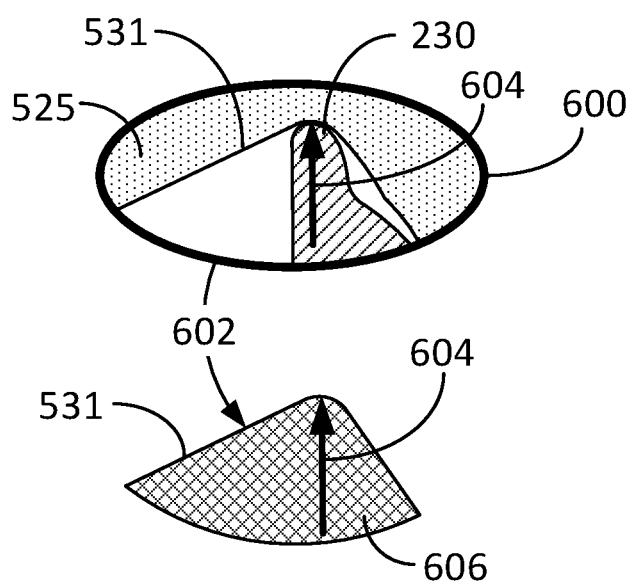
FIG. 6 depicts the "tenting" effect of the leading edge lip consistent with embodiments of the present invention.

FIG. 6 depicts the "tenting" effect of the leading edge lip 230 consistent with embodiments of the present invention. As shown within the elliptical view 600, the inner intestinal wall 531 physically stretches in the direction of the arrow 604 like the fabric of a tent by the leading edge lip 230. Arrow 602 shows just the curved triangular-shaped cross-hatched space 606 created by the leading edge lip 230 pushing against the inner intestinal wall 531 caused by the tenting effect (as shown in the ellipse 600).

Figure 7A:
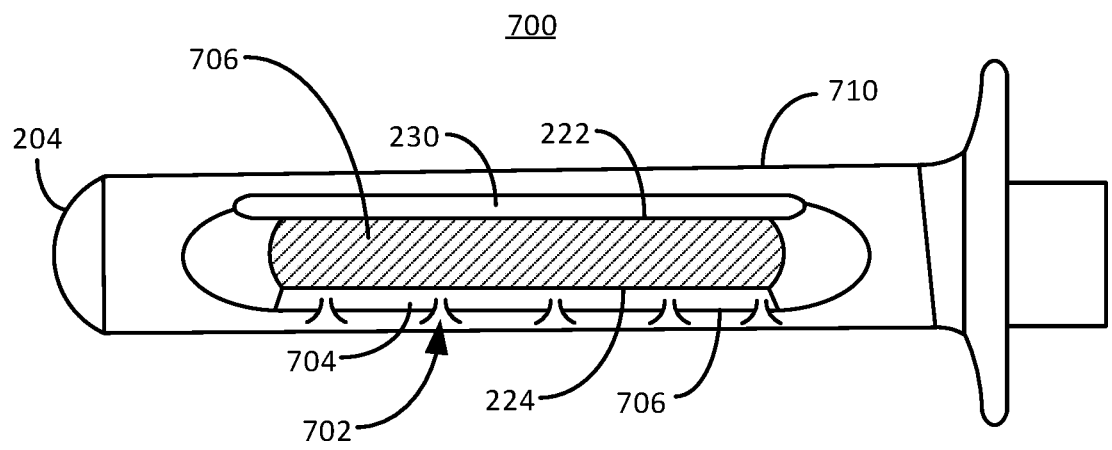
FIGS. 7A and 7B depict line drawings of yet other embodiment of an anal medicinal applicator in accordance with embodiments of the present invention.
Figure 7B:
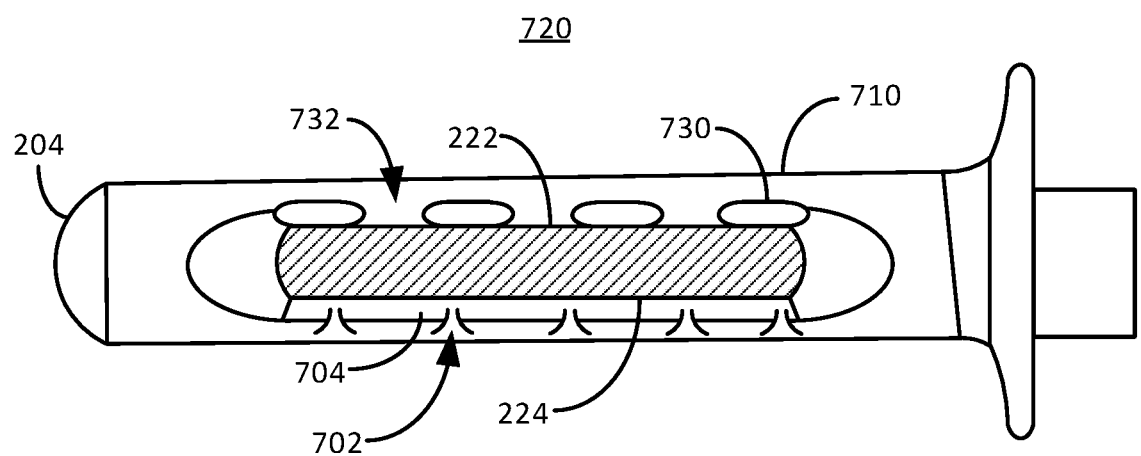

FIGS. 7A and 7B depict line drawings of yet other embodiment of an anal medicinal applicator in accordance with embodiments of the present invention. FIG. 7A depicts a line drawing of an anal medicinal applicator 700 that is similar to the applicator 200 with the exception that the flat trailing edge surface 704 is interrupted by at least one trailing edge channel 702 that provides a pathway for medicinal cream 152 to more easily flow from the longitudinal dispensing slot 706 when expelled therefrom. In other words, each trailing edge channel 702 cuts into the trailing edge 706 of the flat surface 704. In the present embodiment, the trailing edge channels 702 are flared to feather into the surface of the shaft 710. In this way, medicinal cream can more easily flow from the longitudinal slot 706, pass along the outer surface of the shaft 710 and more easily spread on the anal canal. Other channel shapes, sizes and depths that cut into the trailing edge 706 of the flat surface 704 are envisioned within the scope and spirit of the present invention. In this applicator embodiment 700, there is a continuous leading edge lip 230. FIG. 7B depicts a line drawing of an anal medicinal applicator 720 that is similar to the anal medicinal 700 of FIG. 7A except that the leading edge lip 730 is not continuous, i.e., incongruent or interrupted, but rather is separated by a plurality of leading edge channels 732 as shown, i.e., the lip 730 is incongruent or interrupted. This embodiment is considered advantageous to disperse medicinal cream on the surface of an anal canal.

With the present description in mind, some embodiments of the present invention contemplate:

In an anal medicinal applicator embodiment 200, an anal medicinal applicator can comprise: a base 206; a medicinal cream receiving port 201 in the base 206; a shaft 210 extending along an axis 217 from the base 206 and terminating at a dome cap 204, at least one longitudinal slot 220 extending along a portion of the shaft 210, the receiving port 201, the shaft 210 and the at least one longitudinal slot 220 defining an unobstructed pathway 302, the longitudinal slot 220 defined by a leading slot edge 222, a trailing slot edge 224, a proximal slot edge 226, and a distal slot edge 228, the leading slot edge 222 and the trailing slot edge 224 are longer than the proximal slot edge 226 and the distal slot edge 228; and a lip 230 protruding from the shaft 210 along and in-line with at least a portion of the leading slot edge 222.

An additional embodiment of the anal medicinal applicator embodiment 200 is further envisioned wherein the lip 230 is defined by a lip length 213, a lip height 211 and a lip width 215, the lip length 213 extends along the leading slot edge 222, the lip height 211 extends outwardly from a cross-sectional profile of the shaft 161, the lip width 215 extending both orthogonal to the lip height 211 and the lip length 213.

An additional embodiment of the anal medicinal applicator embodiment 200 is further envisioned to comprise at least one channel 732 passing through the lip length 213.

An additional embodiment of the anal medicinal applicator embodiment 200 is further envisioned to comprise essentially a flat surface 704 along the trailing slot edge 224.

An additional embodiment of the anal medicinal applicator embodiment 200 is further envisioned to comprise at least one trailing edge channel 702 passing orthogonally through the flat surface 704.

An additional embodiment of the anal medicinal applicator embodiment 200 is further envisioned to be configured to fixedly link with a medicinal cream dispenser 170 at the receiving port 201, which is further envisioned wherein the medicinal cream dispenser 170 is a medicinal dispenser tube 170.

An additional embodiment of the anal medicinal applicator embodiment 200 is further envisioned wherein the longitudinal slot 220 is in-line with the axis 217.

An additional embodiment of the anal medicinal applicator embodiment 200 is further envisioned to comprise a dome-shaped cap 214 at the distal end 204.

An additional embodiment of the anal medicinal applicator embodiment 200 is further envisioned to comprise an anus abutting stop-plate 208 delineating the base 206 and the shaft 210, the anus abutting stop-plate 208 extending radially beyond the shaft 210.

An additional embodiment of the anal medicinal applicator embodiment 200 is further envisioned wherein the anus abutting stop-plate 208 is circular.

An additional embodiment of the anal medicinal applicator embodiment 200 is further envisioned wherein the anus abutting stop-plate 208 and the base 206 are adapted to remain outside of a human body and the shaft 210 is adapted to penetrate inside of the human body via a human anus 520.

An additional embodiment of the anal medicinal applicator embodiment 200 is further envisioned wherein the anus abutting stop-plate 208 is adapted to be gripped by a human hand.

An additional embodiment of the anal medicinal applicator embodiment 200 is further envisioned wherein the base 206 possesses at least one mechanical feature configured to interface with a medicinal cream dispenser 170 essentially at the receiving port 201.

An additional embodiment of the anal medicinal applicator embodiment 200 is further envisioned wherein the unobstructed pathway 302 is configured to transport a viscous cream 150 from the receiving port 201 and out through the at least one longitudinal slot 220.

An additional embodiment of the anal medicinal applicator embodiment 200 is further envisioned wherein the lip 230 it is adapted to cause a tenting effect 606 on an inner intestinal wall 531.

A method for using an anal medicinal applicator embodiment 200 is envisioned to comprise steps for: providing the anal medicinal applicator 200 that comprises a base 206 possessing a receiving port 201, a shaft 210 extending along an axis 217 from the base 206 to a distal end 204, a probe tip 214 at the distal end 204, at least one longitudinal slot 220 extending along a portion of the shaft 210, an anus abutting stop-plate 208 delineating the base 206 and the shaft 210, the anus abutting stop-plate 208 extending radially beyond the shaft 210, and an unobstructed pathway 302 extending from the receiving port 201 through the anus abutting stop plate 208 and through a portion of the shaft 210 to a distal portion of the at least one longitudinal slot 220 that is closest to the distal end 204, the longitudinal slot 220 defined by a leading slot edge 222, a trailing slot edge 224, a proximal slot edge 226, and a distal slot edge 228, the leading slot edge 222 and the trailing slot edge 224 are longer than the proximal slot edge 226 and the distal slot edge 228, and an intestinal wall tenting lip 230 protruding from the shaft 210 along at least a portion of the leading slot edge 222; inserting the shaft 210 through an anus 520 and into a rectum 528 only as far as the anal abutting stop-plate 208; after the inserting step, dispensing a viscous material 150 through the receiving port 201 and out through the at least one longitudinal slot 220; and after the inserting step, rotating the anal medicinal applicator 200 about the axis 217.

An additional embodiment of the method is further envisioned wherein the shaft 200 is adapted to be manually rotated in the anus 520 in a direction from the leading slot edge 222 to the trailing slot edge 224.

The method is further envisioned to comprise attaching a medicinal dispenser tube 170 to the base 206 to interface the medicinal dispenser tube 170 with the receiving port 201, the dispensing step is accomplished by squeezing the medicinal dispenser tube 170 containing the viscous material 150.

An additional embodiment of the method is further envisioned wherein the viscous material 150 is medicinal cream.

In yet another embodiment of an anal medicinal dispenser 200, the medicinal dispenser 200 can comprise: an anal shaft 210 extending from a handle 206 to an anal tip 204; an anus abutting stop plate 208 extending essentially radially from the anal shaft 210, the anus abutting stop plate 208 delineating the handle 206 from the anal shaft 210; at least one longitudinal slot 220 extending longitudinally along the anal shaft 210; an intestinal wall tenting lip 230 protruding from the anal shaft 210, the intestinal wall tenting lip 230 extending longitudinally along an edge of the longitudinal slot 220; and a medicinal cream pathway 225 extending between and including a) a receiving port 201 in the handle 206 and b) the longitudinal slot 220.

An additional embodiment of the anal medicinal dispenser embodiment 200 is further envisioned wherein the intestinal wall tenting lip 230 protrudes at least 1 mm from the shaft 210 and the intestinal wall tenting lip 230 is less than 7 mm wide.

An additional embodiment of the anal medicinal dispenser embodiment 200 is further envisioned wherein the longitudinal slot 220 extends at least 50% lengthwise along the anal shaft 210, which can further be envisioned wherein the longitudinal slot 220 is defined by a leading edge 222 and a trailing edge 224 that define the longitudinal slot 220 in the lengthwise direction, the intestinal wall tenting lip 230 extends along the leading edge 222.

An additional embodiment of the anal medicinal dispenser embodiment 200 is further envisioned wherein the intestinal wall tenting lip 230 is incongruent 732.

The above embodiments are not intended to be limiting to the scope of the invention whatsoever because many more embodiments are easily conceived within the teachings and scope of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the dispensing slot is linear and extends axially along the length of a shaft other shapes could equally be used while still maintaining substantially the same functionality without departing from the scope and spirit of the present invention. Another example can include providing various other shaped shafts that meet the functionality of spreading medicinal cream in the folds of an anal canal without departing from the scope and spirit of the present invention. Yet another example can include variations of an enlarged dome relative to the shaft diameter within the scope and spirit of the present invention. Another example envisions that a shaft is not limited to being straight (as in FIG. 2A), but may be concave or some other shape so long as the shaft falls within the scope and spirit of the present invention. Different shape lips are envisioned within the scope and spirit of the present invention. Channels of various sorts are envisioned along the leading slot edge through the lip. Discontinuous lips are envisioned along the leading slot edge. Other shaped surfaces, such as roll-off surfaces are envisioned at the trailing slot edge without departing from the scope and spirit of the present invention. Various shaped channels are envisioned extending through the trailing slot edge without departing from the scope and spirit of the present invention. Various dispenser apparati can be used with the anal medicinal applicator embodiments within the scope and spirit of the present invention. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the claims of the invention disclosed.

What is claimed is:

1. An anal medicinal applicator comprising:
   a base;
   a medicinal cream receiving port in the base;
   a shaft extending along an axis from the base and terminating at a dome cap;
   at least one longitudinal slot extending along a portion of the shaft;
   a shaft outer profile that includes neither the portion of the shaft nor the dome cap;
   the at least one longitudinal slot comprising a leading edge and a trailing edge,
   the leading edge comprising a raised lip protruding from the shaft outer profile;
   the trailing edge either in line with or recessed from the shaft outer profile.

2. The anal medicinal applicator of claim 1 wherein the lip is defined by a lip length, a lip height and a lip width, the lip length extends along the leading edge, the lip height extends outwardly from the shaft outer profile, the lip width extending both orthogonal to the lip height and the lip length.

3. The anal medicinal applicator of claim 2 further comprising at least one channel passing through the lip length.

4. The anal medicinal applicator of claim 1 further comprising essentially a flat surface along the trailing edge.

5. The anal medicinal applicator of claim 4 further comprising at least one trailing edge channel passing orthogonally through the flat surface.

6. The anal medicinal applicator of claim 1 is configured to fixedly link with a medicinal cream dispenser 170 at the receiving port.

7. The anal medicinal applicator of claim 1 further comprising an anus abutting stop-plate delineating the base and the shaft, the anus abutting stop-plate extending radially beyond the shaft.

8. The anal medicinal applicator of claim 1 wherein the shaft is configured to transport a viscous cream from the receiving port and out through the at least one longitudinal slot.

9. The anal medicinal applicator of claim 1 wherein the lip it is adapted to cause a tenting effect on an inner intestinal wall.

10. The anal medicinal applicator of claim 1 further comprising the dome cap at a distal end of the shaft.

11. The anal medicinal applicator of claim 1 wherein the shaft and the base are separated by an anus abutting stop-plate, the base and anus abutting stop-plate are adapted to remain outside of a human body and the shaft is adapted to penetrate inside of the human body via a human anus.

12. A method for using a medicinal applicator, the method comprising:
- providing the medicinal applicator that comprises a base possessing a receiving port, a shaft extending along an axis from the base to a distal end,
- a probe tip at the distal end, at least one longitudinal slot extending along a portion of the shaft,
- an anus abutting stop-plate delineating the base and the shaft, the anus abutting stop-plate extending radially beyond the shaft, and
- an unobstructed pathway extending from the receiving port through the anus abutting stop-plate and through the at least one longitudinal slot, the at least one longitudinal slot comprising a leading slot edge and a trailing slot edge, and
- a shaft outer profile that includes neither the portion of the shaft nor the probe tip,
- the trailing slot edge either in line with or recessed from the shaft outer profile,
- a lip protruding from the shaft outer profile along at least a portion of the leading slot edge;
- inserting the shaft through an anus and into a rectum only as far as the anus abutting stop-plate;
- after the inserting step, dispensing a viscous material through the receiving port and out through the at least one longitudinal slot; and
- after the inserting step, rotating the medicinal applicator about the axis.

13. The method of claim 12 wherein the shaft is adapted to be manually rotated in the anus in a direction from the leading slot edge to the trailing slot edge.

14. The method of claim 12 further comprising attaching a medicinal dispenser tube to the base to interface the medicinal dispenser tube with the receiving port, the dispensing step is accomplished by squeezing the medicinal dispenser tube containing the viscous material.

15. The method of claim 12 wherein the viscous material is medicinal cream.

16. A medicinal applicator comprising:
- a shaft extending from a handle to a tip;
- at least one longitudinal slot extending longitudinally along a portion of the shaft, the at least one longitudinal slot comprising a leading edge and a trailing edge;
- a shaft outer profile that includes neither the portion of the shaft nor the tip;
- the leading edge comprising a raised lip protruding from the shaft outer profile, the trailing edge either in line with or recessed from the shaft outer profile; and
- a medicinal cream pathway extending between and including a) a receiving port in the handle and b) the at least one longitudinal slot.

17. The anal medicinal applicator of claim 16 wherein the lip protrudes at least 1 mm from the shaft outer profile and the lip is less than 7 mm wide.

18. The anal medicinal applicator of claim 16 wherein the at least one longitudinal slot extends at least 50% lengthwise along the shaft.

19. The anal medicinal applicator of claim 16 wherein the shaft outer profile is defined by a circular shape.

20. The anal medicinal applicator of claim 16 wherein the lip is incongruent.

\* \* \* \* \*